(12) United States Patent
Cai et al.

(10) Patent No.: US 11,620,745 B2
(45) Date of Patent: Apr. 4, 2023

(54) METHOD AND SYSTEM FOR HARVESTING LESION ANNOTATIONS

(71) Applicant: Ping An Technology (Shenzhen) Co., Ltd., Shenzhen (CN)

(72) Inventors: Jinzheng Cai, Bethesda, MD (US); Adam P Harrison, Bethesda, MD (US); Ke Yan, Bethesda, MD (US); Yuankai Huo, Bethesda, MD (US); Le Lu, Bethesda, MD (US)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 345 days.

(21) Appl. No.: 16/984,727

(22) Filed: Aug. 4, 2020

(65) Prior Publication Data

US 2021/0224981 A1 Jul. 22, 2021

Related U.S. Application Data

(60) Provisional application No. 62/962,268, filed on Jan. 17, 2020.

(51) Int. Cl.
*G06T 7/00* (2017.01)
*G06T 5/50* (2006.01)
*G06T 19/20* (2011.01)

(52) U.S. Cl.
CPC .............. *G06T 7/0012* (2013.01); *G06T 5/50* (2013.01); *G06T 19/20* (2013.01);
(Continued)

(58) Field of Classification Search
CPC ......... G06T 7/0012; G06T 5/50; G06T 19/20; G06T 2207/30096; G06T 2210/12; G06T 2219/004; G06T 7/0002; G06T 2207/20; G06T 2207/20081; G06T 2207/20084; G06T 2207/10; G06T 2207/10072; G06T 2207/10081; G06T 2007/10072; G06T 2207/10088; G16H 30/00; G16H 30/40; G16H 50/00; G16H 50/20; G06V 2201/00; G06V 2201/03; G06K 2209/00;
(Continued)

(56) References Cited

U.S. PATENT DOCUMENTS

2019/0385018 A1* 12/2019 Navari et al. ........ G06K 9/6256
382/103

FOREIGN PATENT DOCUMENTS

WO  WO-2019/103912 A2 * 5/2019 ........... G06T 7/0012
WO  WO-2019/238804 A1 * 12/2019 ........... G06T 7/0012

* cited by examiner

*Primary Examiner* — Gandhi Thirugnanam
*Assistant Examiner* — Mychal J Gibbens
(74) *Attorney, Agent, or Firm* — Anova Law Group, PLLC

(57) ABSTRACT

A method of harvesting lesion annotations includes conditioning a lesion proposal generator (LPG) based on a first two-dimensional (2D) image set to obtain a conditioned LPG, including adding lesion annotations to the first 2D image set to obtain a revised first 2D image set, forming a three-dimensional (3D) composite image according to the revised first 2D image set, reducing false-positive lesion annotations from the revised first 2D image set according to the 3D composite image to obtain a second-revised first 2D image set, and feeding the second-revised first 2D image set to the LPG to obtain the conditioned LPG, and applying the conditioned LPG to a second 2D image set different than the first 2D image set to harvest lesion annotations.

14 Claims, 12 Drawing Sheets

(52) U.S. Cl.
CPC .................. *G06T 2207/30096* (2013.01);
*G06T 2210/12* (2013.01); *G06T 2219/004* (2013.01)

(58) Field of Classification Search
CPC ........ G06K 2209/05; G06K 9/20; G06K 9/32; G06K 9/3233; G06K 9/3241; G06K 9/62; G06K 9/6217; G06K 9/6256; G06K 9/6259; G06K 9/6267; G06K 9/6279; G06K 9/628; G06K 9/6288; G06K 9/6292; G06N 3/0454; G06N 3/08; G06N 3/084
See application file for complete search history.

S210.4

ADDING 2D BOUNDING BOXES
OVER LESION ANNOTATIONA IN REVISED
FIRST 2D IMAGE SET
S310

↓

STACKING REVISED FIRST 2D IMAGE SET
S320

↓

FUSING 2D BOUNDING BOXES AFTER
STACKING TO OBTAIN 3D BOUNDING BOXES
S330

↓

DETERMINING ANNOTATIONS AS TRUE
POSITIVE VIA COMPARISON BETWEEN
2D & 3D BOUNDING BOXES
S340

FIG. 3 a. RECIST mark    b. Harvested Lesion    c. 3D Box

METHOD AND SYSTEM FOR HARVESTING LESION ANNOTATIONS

CROSS-REFERENCE TO RELATED APPLICATION

This application claims the priority of U.S. Provisional Patent Application No. 62/962,268, filed on Jan. 17, 2020, the entire contents of which are incorporated herein by reference.

TECHNICAL FIELD

The present disclosure relates to a technical field of medical image processing and, more specifically, to methods and systems for harvesting lesion annotations.

BACKGROUND

Paralleling developments in computer vision recent years have ushered the emergence of large-scale medical image databases. These databases are helping to meet the data-hungry needs of deep learning and to advance medical imaging analysis research. Yet, many of these databases are collected retrospectively from hospital picture archiving and communication system (PACS), which host the medical images and text reports from daily radiological workflows. While PACS are a rich source of large-scale medical imaging data, such data may often be ill-suited for training machine learning systems, because the data are not curated from a machine learning perspective. As a result, many of these large-scale medical imaging datasets suffer from uncertainties, mis-annotations, and incomplete annotations.

The disclosed methods and systems are directed to solve one or more problems set forth above and other problems.

SUMMARY

In one aspect of the present disclosure, a method of harvesting lesion annotations includes conditioning a lesion proposal generator (LPG) based on a first two-dimensional (2D) image set to obtain a conditioned LPG, including adding lesion annotations to the first 2D image set to obtain a revised first 2D image set, forming a three-dimensional (3D) composite image according to the revised first 2D image set, reducing false-positive lesion annotations from the revised first 2D image set according to the 3D composite image to obtain a second-revised first 2D image set, and feeding the second-revised first 2D image set to the LPG to obtain the conditioned LPG, and applying the conditioned LPG to a second 2D image set different than the first 2D image set to harvest lesion annotations.

In another aspect of the present disclosure, a lesion imaging system includes a lesion proposal generator (LPG) for harvesting lesion annotations, the LPG including a memory and a processor coupled to a memory, the processor is configured to perform conditioning a lesion proposal generator (LPG) based on a first two-dimensional (2D) image set to obtain a conditioned LPG, including adding lesion annotations to the first 2D image set to obtain a revised first 2D image set, forming a three-dimensional (3D) composite image according to the revised first 2D image set, reducing false-positive lesion annotations from the revised first 2D image set according to the 3D composite image to obtain a second-revised first 2D image set, and feeding the second-revised first 2D image set to the LPG to obtain the conditioned LPG, and applying the conditioned LPG to a second 2D image set different than the first 2D image set to harvest lesion annotations.

In yet another aspect of the present disclosure, a non-transitory computer-readable storage medium is provided for storing a plurality of instructions, wherein when the plurality of instructions are executed by a processor, cause the processor to perform conditioning a lesion proposal generator (LPG) based on a first two-dimensional (2D) image set to obtain a conditioned LPG, including adding lesion annotations to the first 2D image set to obtain a revised first 2D image set, forming a three-dimensional (3D) composite image according to the revised first 2D image set, reducing false-positive lesion annotations from the revised first 2D image set according to the 3D composite image to obtain a second-revised first 2D image set, and feeding the second-revised first 2D image set to the LPG to obtain the conditioned LPG, and applying the conditioned LPG to a second 2D image set different than the first 2D image set to harvest lesion annotations.

BRIEF DESCRIPTION OF THE DRAWINGS

FIG. 3 is a schematic flow chart diagram of a fusing process according to one or more embodiments of the present disclosure;

DETAILED DESCRIPTION

In view of the below descriptions of embodiments of the present disclosure in conjunction with the accompanying drawings, aspects, advantages, and prominent features of the present disclosure will become readily apparent to those skilled in the art.

Acquiring large-scale medical image data is in general intractable, due to prohibitive expert-driven annotation costs. Recent datasets extracted from hospital archives, for example, DeepLesion, which includes annotations to some extent, have begun to address this problem. However, to the extent annotations are present in existing DeepLesion image slices, these annotations only represent a very small percent of annotatable lesions, many of these annotations are incomplete, and vast majority of lesions are believed to remain un-annotated.

The present disclosure, in one or more embodiments, provides a method, a system, and a non-transitory storage medium for harvesting lesion annotations from the Deep-Lesion dataset, or any other suitable datasets. In one or more embodiments, a subset of the DeepLesion dataset is randomly selected, a portion of the subset is manually annotated by board-certified clinicians such as radiologists to generate an annotation-enhanced subset of medical image volumes, and this annotation-enhanced subset is then used to mine annotations from the remainder of the subset, where the remainder is not subject to the enhanced annotation by the board-certified clinicians.

In certain embodiments, a reasonably sensitive lesion proposal generator (LPG) and a selective lesion proposal classifier (LPC) may be employed in integration. Any suitable LPG and any suitable LPC or suitable equivalent devices may be employed for this integration. The performance of harvesting lesion annotations is believed to be improved via the LPG or an integration of LPG with LPC or any suitable equivalent devices thereof, where the LPG and the LPC when integrated together may help produce harvested and hard negative annotations, which are in turn re-used to finetune the LPG and the LPC. This fine-tuning is continued until no extra lesions beyond a preset threshold are found. In certain embodiments, the preset threshold may be zero.

According to one or more embodiments of the present disclosure, the term "proposal" as referenced in the LPG (lesion proposal generator) and the LPC (lesion proposal classifier) may be understood as lesion annotations proposed by the LPG and/or LPC. In certain embodiments, the LPG may be referred to as lesion annotation generator and the LPC may be referred to as lesion annotation classifier.

Figure 1:
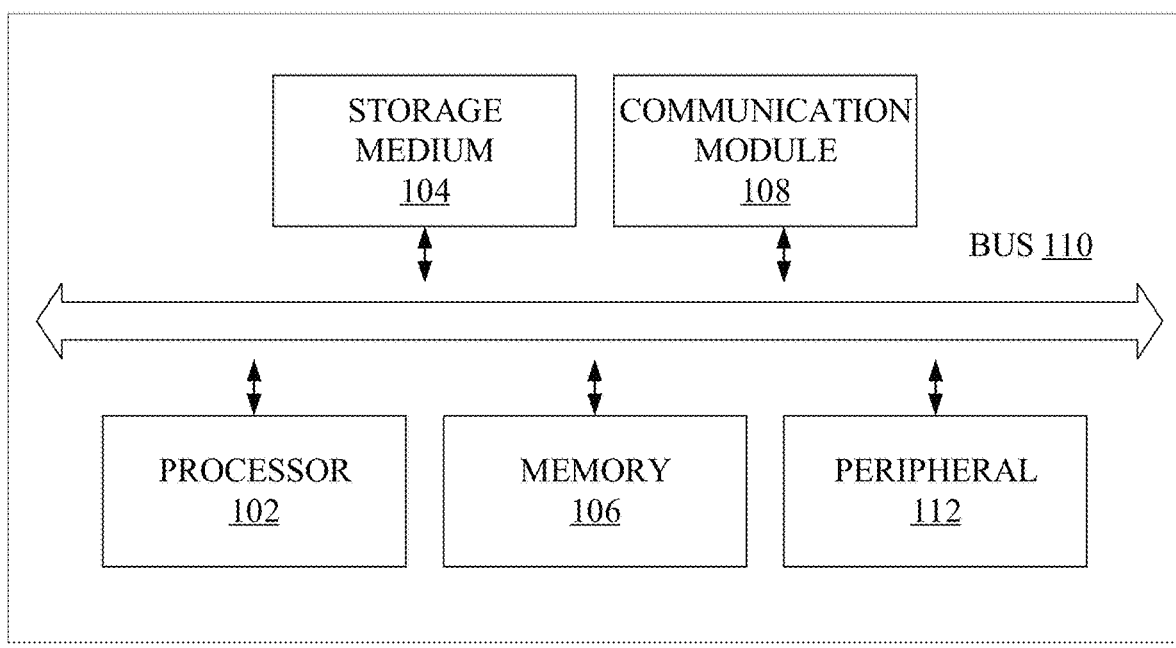
FIG. 1 is a schematic structural diagram of an apparatus according to one or more embodiments of the present disclosure.

According to one embodiment of the present disclosure, FIG. 1 is a schematic diagram of an apparatus 100 for performing lesion annotation method such as a method 200A of FIG. 2A or method 200B of FIG. 2B to be detailed below. The apparatus 100 may be a computing device including a memory 106 and a processor 102 coupled to the memory 106, the processor 102 being configured to perform a method of harvesting lesion annotations such as method 200A of FIG. 2A and/or in association with FIG. 2B, FIG. 3, FIG. 4, FIG. 5, and/or FIG. 6 to be detailed below. In certain embodiments, the apparatus 100 may be an LPG or an LPG in working integration with an LPC.

The apparatus 100 may also include a non-transitory storage medium 104 including instructions (not shown) which cause the processor 102 to perform a method of harvesting lesion annotations such as the method 200A of FIG. 2A and/or in association with FIG. 2B, FIG. 3, FIG. 4, FIG. 5, and/or FIG. 6 to be detailed below. The apparatus 100 may further include a communication module 108 and peripheral devices 112, as necessary. All components 102, 104, 106, 108, and 112 may be in data communication with a bus 110. Certain components may be omitted, and other components may be included.

According to another embodiment of the present disclosure, and as mentioned above in connection with FIG. 1, FIG. 2A is a schematic flow diagram of the method 200A of harvesting lesion proposals. In general, the method 200A embodies the task of producing as high-quality lesion candidates as possible, via a lesion proposal generator (LPG). Any state-of-the art detection system may operate as an LPG; however, there are attributes of an LPG that may receive particular attention due to benefits these attributes deliver. For example, an LPG with high sensitivity helps recover unlabeled lesions. Meanwhile, if it retains reasonable specificity, it makes downstream classification of proposals into true- and false-positives much more feasible. Computational efficiency may also be a consideration, to not only make training scalable, but also to be efficient in processing large amounts of computed tomography (CT) scan images. Finally, simplicity and efficiency are also attributes of a good LPG that are worth consideration, as the LPG may just be one component in a larger system.

For the purpose of describing the method 200A of harvesting lesion annotations, and in certain embodiments, a set of N number of original CT volumes, V, along with two-dimensional (2D) response evaluation criteria in solid tumors (RECIST) marks or annotations for each volume, R, is randomly selected from the original DeepLesion dataset. N may be of any suitable numbers available from the DeepLesion dataset, and a subset of N, namely $N_M$, is selected to be given enhanced annotation by the radiologist, where $N_M \ll N$ to keep the manual annotation cost at a manageable level. In certain embodiments, the $N_M$ is within a range of no less than 50, 10, 150, 200, or 250, and no greater than 5,000, 4,000, 3,000, or 2,000. Each volume is associated with a set of lesions $l_k$, where $l_k^R$ and $l_k^U$ denote the RECIST-annotated and unannotated lesions, respectively. Uppercase is used to denote sets taken across the dataset, for example, $L_U$. One of the goals is to harvest a set of 3D lesion bounding boxes, $P_H^+$, that would cover 2D RECIST marks for $L_U$, had they been available.

Figure 12:
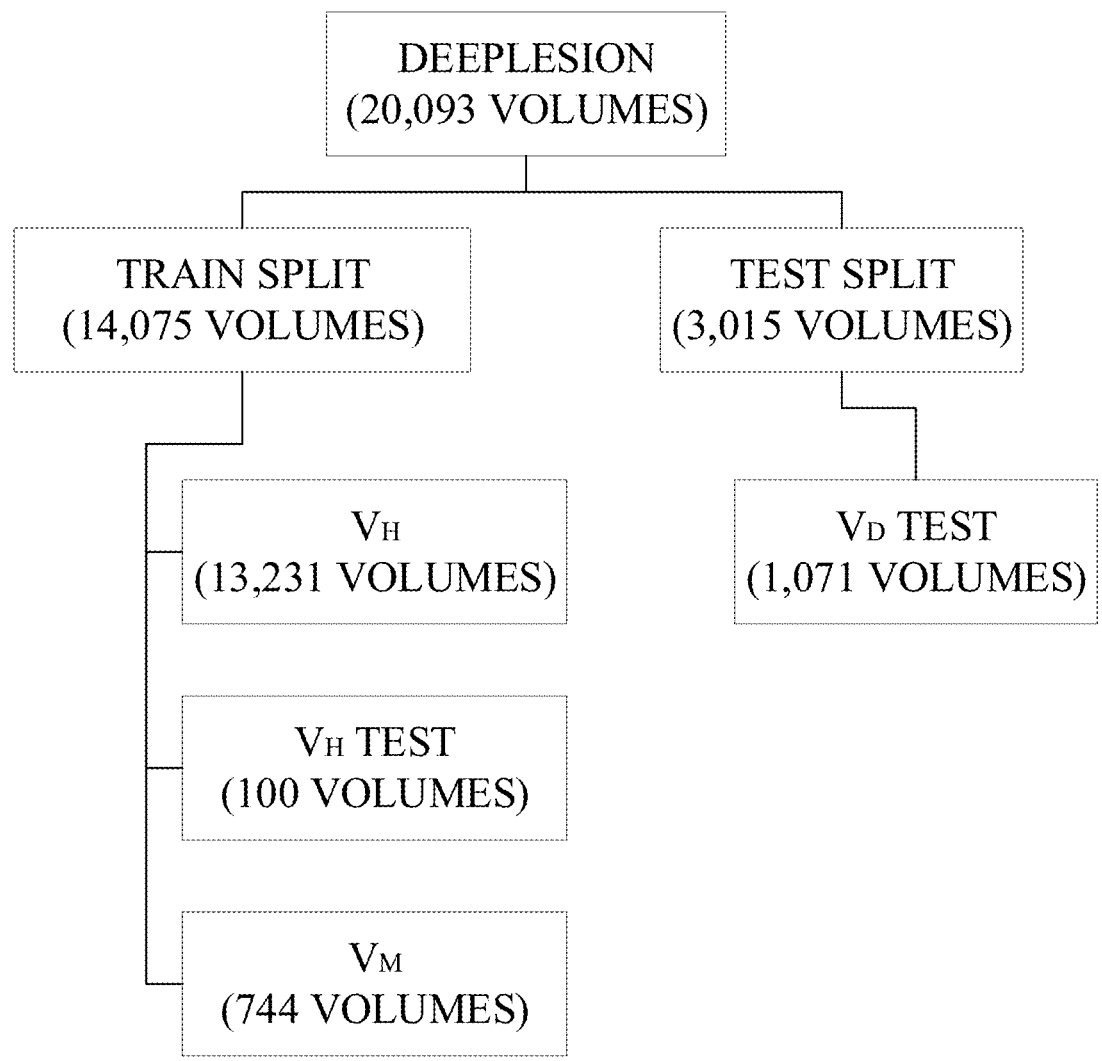
FIG. 12 is a schematic diagram of a source data image split according to one or more embodiments of the present disclosure.

In certain embodiments, and further in view of FIG. 12, about 20,093 CT volumes are available from the DeepLesion database, which is divided to a training set of 14,075 volumes and a test set of 3,015 volumes. The training set includes three subsets, namely a $V_H$ set of 13,231 volumes, a $V_M$ set of 744 volumes, and a $V_H^{test}$ ($V_H$ test) of 100 volumes. The $V_M$ set includes the $N_M$ of 744 volumes, which are given the enhanced annotation performed by the radiologist. The N, referred in the relationship of $N_M \ll N$, may be the DeepLesion set of 20,093 volume or may be the $V_H$ set of 13,231 volumes. The $V_H$ set of 13,231 volumes is not given the enhanced annotation, and is the set from which annotation proposals are to be generated using the harvesting method detailed below, where the generate annotations proposals are employed in training the harvesting model. Of the test set of 3,015 volumes, the $V_D^{test}$ of 1,071 volumes is employed to testing the annotation harvesting method for recall and precision evaluations, as detailed below.

In certain embodiments, an image such as a CT image obtained from the DeepLesion database is often a 3D presentation depicting one or more lesions in a 3D configuration. Each such image may be considered a volume. Each such image or volume includes many image slices and each such image slice may be considered a 2D presentation.

In certain embodiments, images such as images obtained from the DeepLesion database come with marks previously entered during their corresponding hospital or clinical procedures. These marks may come in the shape of a cross optionally with a color other than a color of black. These marks may be called RECIST marks, or original RECIST marks, or original marks. A non-limiting example of these marks is found in FIG. 9A (the cross without a bounding box) and in FIG. 9B (the cross with a bounding box).

In certain embodiments, additional lesions may be discovered on those images obtained from databases such as DeepLesion, through manual inspection and marking by a professional such as a physician and/or a radiologist. Through the additional inspection and marking, more lesions may be found on these images and hence these images are afforded greater data-mining values and potentials.

In certain embodiments, the word "label" may refer to all marks on the images and/or the action of marking or adding marks on the images.

Figure 4:
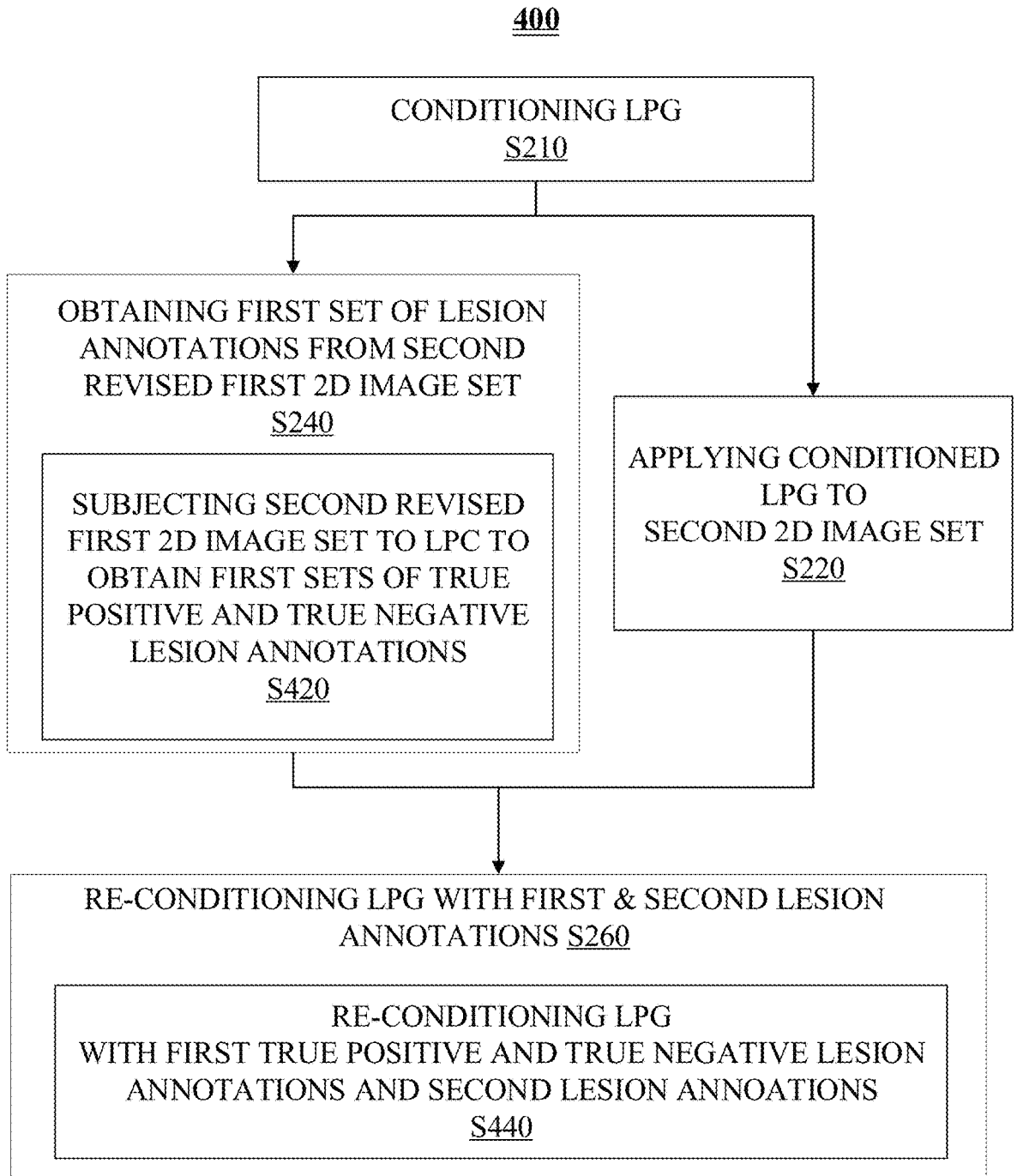
FIG. 4 is a schematic flow chart diagram of another model-training method according to one or more embodiments of the present disclosure.
Figure 5:
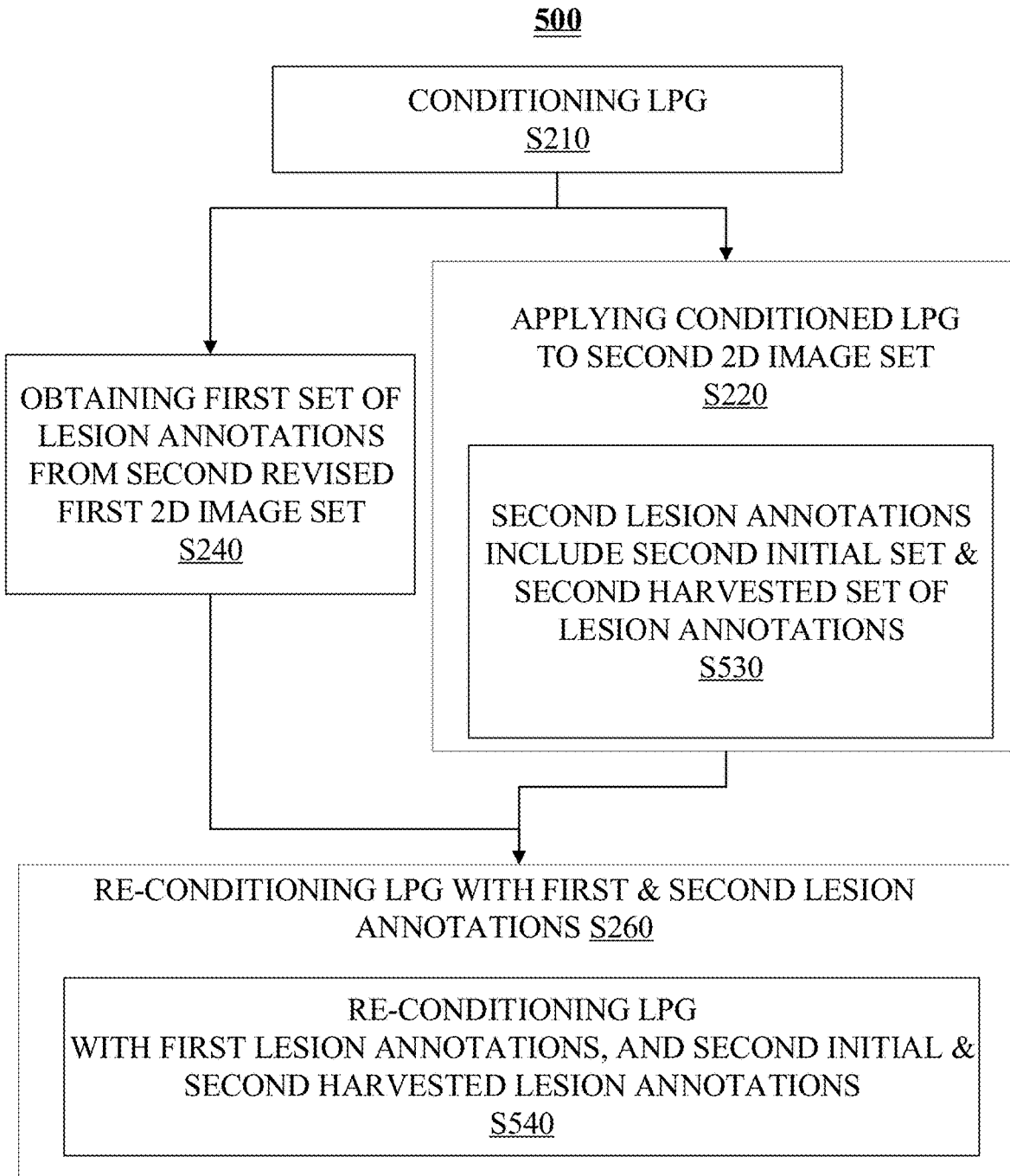
FIG. 5 is a schematic flow chart diagram presenting a modification or addition to the method of FIG. 2 according to one or more embodiments of the present disclosure.
Figure 6:
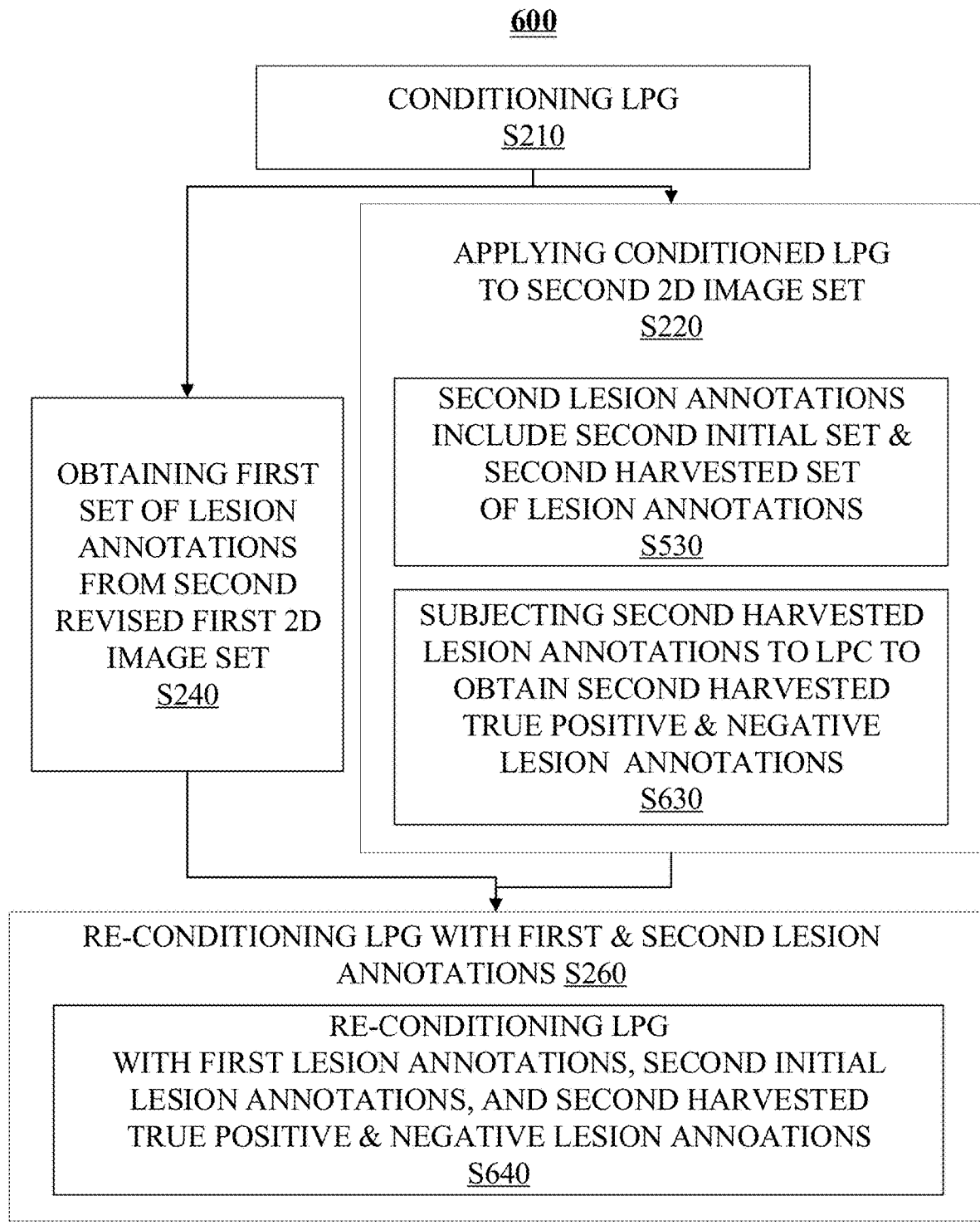
FIG. 6 is a schematic flow chart diagram presenting a modification or addition to the method of FIG. 2 according to one or more embodiments of the present disclosure.

In certain embodiments, the term "proposal" refers to an area of interest generated by the method of FIG. 2A, FIG. 2B, FIG. 3, FIG. 4, FIG. 5, and/or FIG. 6 that is indicative of the presence of a lesion on the image. In certain instances, the proposal may be a true positive meaning the area of interest as indicated by the proposal points to the presence of a lesion. In certain other instances, the proposal may be a false positive, in that the area of interest is a false indication of a lesion.

In certain embodiments, the term "annotation" may collectively refer to all marks, all labels, and/or all proposals. Alternatively, the term "marks," the term "labels," the term "proposals," and the term "annotations" may be used interchangeably.

At step S210, an LPG is conditioned based on a first two-dimensional (2D) image set to obtain a conditioned LPG. In certain embodiments, the conditioned LPG is also termed a "2.5D-LPG" to reflect a process integration of an initial LPG coupled with a 2D fuser such as MULAN fuser, where 2D image slices are fused to form a 3D composite image. Any suitable LPG may be used as the initial LPG from which the 2.5D-LPG may be formed. In one embodiment, 2.5D-CenterNet is employed as the initial LPG. In most cases, lesions have convex shapes which have centroids located inside the lesions. 2.5D-CenterNet is a suitable choice as the initial LPG as 2.5-CenterNet detects center points in lesions and regresses their width and length.

To detect the center points, center points "c" are extracted for each lesion and a low-resolution counterpart, c', is computed based on the down-sampling process used to compute the output feature map. Center points may then be splatted onto a heatmap using a Gaussian kernel. If two Gaussians of the same class overlap, the element-wise maximum is taken. The training objective is to then produce a heatmap using a penalty-reduced pixel-wise logistic regression with focal loss $$L_k = \frac{-1}{m} \sum_{xy} \begin{cases} (1 - Y_{xy})^\alpha \log(\hat{Y}_{xy}) & \text{if } Y_{xy} = 1 \\ (1 - Y_{xy})^\beta (\hat{Y}_{xy})^\alpha & \text{otherwise} \\ \log(2 - \hat{Y}_{xy}) & \end{cases},$$

where m is the number of objects in the slice and a and p are hyper-parameters of the focal loss. At every output pixel, the width, height, and offset of lesions are also regressed. Any suitable center points calculation algorithms may be employed for the purpose of generating 2D and 3D bounding boxes.

In certain embodiments, the term "train" or "training" may refer to conditioning an LPG to obtain a conditioned or re-conditioned LPG, or to conditioning an LPC to obtain a conditioned or reconditioned LPC.

With the 2.5D-LPG, 2D bounding boxes as present on each of the 2D image slices may fuse to form 3D bound boxes in the fused 3D composite image. Accordingly, lesion annotations harvested from the 2.5D-LPG are not only additionally identified, but also indicated with 3D bounding boxes, which readily and favorably potentiates any next-step analysis. For the purpose of step S210 of the method 200A or method 2B, the first 2D image set may be a small piece of dataset randomly selected from a much larger dataset, such as DeepLesion. The randomly selected small piece of dataset is of a manageable volume size to enable manual annotations by a field expert such as a board-certified radiologist. According to certain embodiments, a dataset in a sampling number of 744 volumes randomly selected from the DeepLesion is a non-limiting example of the first 2D image set. It should be noted the volume set of the first 2D image set should not be a factor limiting the applicability of the method 200A or 200B. In fact, the volume size (N volumes) of the first 2D image set may vary based on a given project at hand. For example, the dataset of 744 volumes may be expanded to a much larger volume size if expert cost associated with manual annotations is not a limiting factor. However, a clear benefit associated with the employment of the first 2D image set in the method of 200A or 200B is to allow a reasonably manageable spending on a small subset of a very larger dataset such as DeepLesion to obtain an annotation-enhanced image dataset which is then used to train an LPG, denoted the 2.5D-LPG, that is then used to harvest annotations on raw image dataset at scale.

The step S210 of building the conditioned LPG may include one or more of sub-step S210.2, sub-step S210.4, sub-step S210.6, and sub-step S210.8 detailed below.

At sub-step S210.2, lesion annotations are added to the first 2D image set to obtain a revised first 2D image set. The CT volumes V include an annotation-enhanced subset of $N_M$ volumes, $V_M$. Such volumes can be generated by supplementing the original DeepLesion RECIST marks for $V_M$. As described above, the first 2D image set may be a subset randomly selected from the DeepLesion dataset before any additional annotations are entered by the board-certified radiologist recruited for the specific project of annotation enhancement. The second 2D image set, such as the remainder of volumes from which additional annotations are harvested are denoted $V_H$, where $V_M$ is exploited to harvest lesions from $V_H$. As with the first 2D image set, the second 2D image set may be of any suitable volume size. For cost considerations, the second 2D image set, such as the $V_H^{test}$ set of 100 volumes referenced in FIG. 12, may be of a volume number smaller than the first 2D image set, and in some other embodiments, the Second 2D image set may be of a total number larger than the number of the first 2D image set, such as the $V_H$ set of 13,231 referenced in FIG. 12. In a major difference, the second 2D image set has not seen or been subjected to manual annotations by the board-certified radiologists, unlike the first 2D image set. The idea is to condition LPG using the annotation-enhanced first 2D image set and then apply the conditioned LPG to the second 2D image set to harvest lesion annotations not previously reported in the DeepLesion database.

While the first 2D image set may be of any suitable image count, the image count of the first 2D image set is kept at a number, such as $N_M << N$ to keep labor requirements low. In the embodiments described below, the 744 volumes set that is annotation-enhanced accounts for merely about 5.3% of the total volume set in the DeepLesion database. In certain embodiments, the first 2D image set is no more than 15%, no more than 12.5%, no more than 10%, no more than 7.5%, and no more than 5% in volumes of a larger image set such as DeepLesion. Of course, the first 2D image set includes at least one image, a meaningful lower end regarding its volumes size may be greater than 0.05%, greater than 0.1%, greater than 1% or greater than 1.5%.

DeepLesion is a medical image database that covers various tumors, lymph nodes, and other key findings, which are minded from computed tomography (CT) scans from the US National Institutes of Health Clinical Center (PACS). The mined lesions are extracted from response evaluation criterial in solid tumors (RECIST) marks performed by clinicians to measure tumors in their daily workflow. Currently DeepLesion contains retrospectively clinically annotated lesions from about 10,594 CT scans of 4,427 unique patients. A variety of lesion types and subtypes have been included in this database, such as lung nodules, liver tumors, and enlarged lymph nodes. As such, the DeepLesion dataset is a source of data for medical imaging analysis tasks, including training and characterizing lesion detectors and for developing radiomics-based biomarkers for tumor assessment and tracking.

Sub-step S210.2 may start by conditioning or training a 2D lesion proposal generator (LPG) using the original RECIST marks, R. To keep the framework flexible, any state-of-the-art lesion detection system may be used, either an off-the-shelf variant or the customized and enhance approached described herein elsewhere. After convergence, the trained LPG is executed on V, using the 2D to 3D scheme such as the scheme described in relation to FIG. 8, to produce a set of lesion proposals, PG. The thus produced set of lesion proposals PG likely cover a large number of L, but they may suffer from high false positive rates. To correct this, PG is divided into $P_M$ and $P_H$, which are those respectively proposed from $V_M$ and $V_H$, which correspond respectively to the first 2D image set and the second 2D image set.

In one or more embodiments, the term "proposal," "proposals," "mark," or "marks" may refer to lesion annotation or lesion annotations in relation to the lesion images.

At sub-step S210.4, a 3D composite image is formed according to the revised first 2D image set. The revised first 2D image set may be fused or integrated to form a three-dimensional (3D) composite image. The revised first 2D image set may be the first 2D image set with annotations added via manual annotations performed by the board-certified radiologists. While the first 2D image set is part of the DeepLesion database, the revised 2D image set is not.

DeepLesion is a non-limiting example of an original image dataset from which the first and second 2D image sets may be derived. One or more embodiments of the present disclosure works to harvest missing or additional annotations from the otherwise incomplete DeepLesion dataset. Accordingly, 3D annotations may then be generated from the thus produced 2D RECIST marks or annotations. While 3D annotations often provide greater clarity in lesion discovery, current DeepLesion works operate and evaluate only based on the 2D RECIST marks on 2D slices that happen to contain the marks. This may be problematic, as RECIST-based evaluation may not correctly reflect actual performance. The 2D evaluation may miscount true positives on an adjoining slice as false positives. Moreover, automated methods should process the whole image volume rather than only the slices containing RECIST marks, meaning precision should be correlated to false positives per volume rather than per selected image slices, which may not be clinically ideally desirable.

An approach to create 3D bounding boxes from 2D slice-wise detections, according to one or more embodiments of the present disclosure, helps realize evaluation of proposals in 3D to overcome problems associated with evaluating proposal only from 2D.

To accomplish the from the 2D to the 3D or "2D-to-3D" scheme and thus to generate the 2.5D LPG, and in certain embodiments, an LPG is applied to each axial slice of a volume, which is a 2D slice such as one in the first or second 2D image set. In certain embodiments, only proposals or annotations with objectiveness scores over a certain threshold are considered. Such threshold may be of any suitable value and may be varied according to an end goal of a given annotation project. Next, proposals in consecutive slices are stacked using a suitable method such as Kalman Filter-based tracker. Basically, the tracker stacks proposals basing on their 2D intersection over union (IoU) being greater or equal to 0.5, creating a 3D bounding box $(x_1', x_2', y_1', y_2', z_1', z_2')$. The IoU may be of any suitable values, including but not limited to a value of greater or equal to 0.5. To measure performance, 2D bounding boxes may be generated based on the extents of the RECIST marks, $(x_1, x_2, y_1, y_2, z_1, z_2)$, where z is the slice containing the mark. The 3D box is counted as a true positive if, in certain embodiments, $z_1' \leq z_2'$ and IoU $((x_1, x_2, y_1, y_2), (x_1', x_2', y_1', y_2')) \geq 0.5$. Otherwise, it may be considered a false positive. IoU may vary dependent upon a give project at hand. In certain embodiments, IoU is of a range of between 0 and 1, inclusive, or more particularly, a range of between 0.5 and 0.9, inclusive.

Employment of the 2.5D-LPG or the conditioned or re-conditioned LPG, according to one or more embodiments of the present disclosure, helps avoid resorting to a full and direct 3D LPG. While a full and direct 3D LPG may be informational, it however comes with prohibitive memory and computational demands. With the employment of 2.5D-LPG, where the 3D context is engineered by fusing 2D slices, annotations may be recalled at a reasonable cost of labor and memory.

Figure 7:
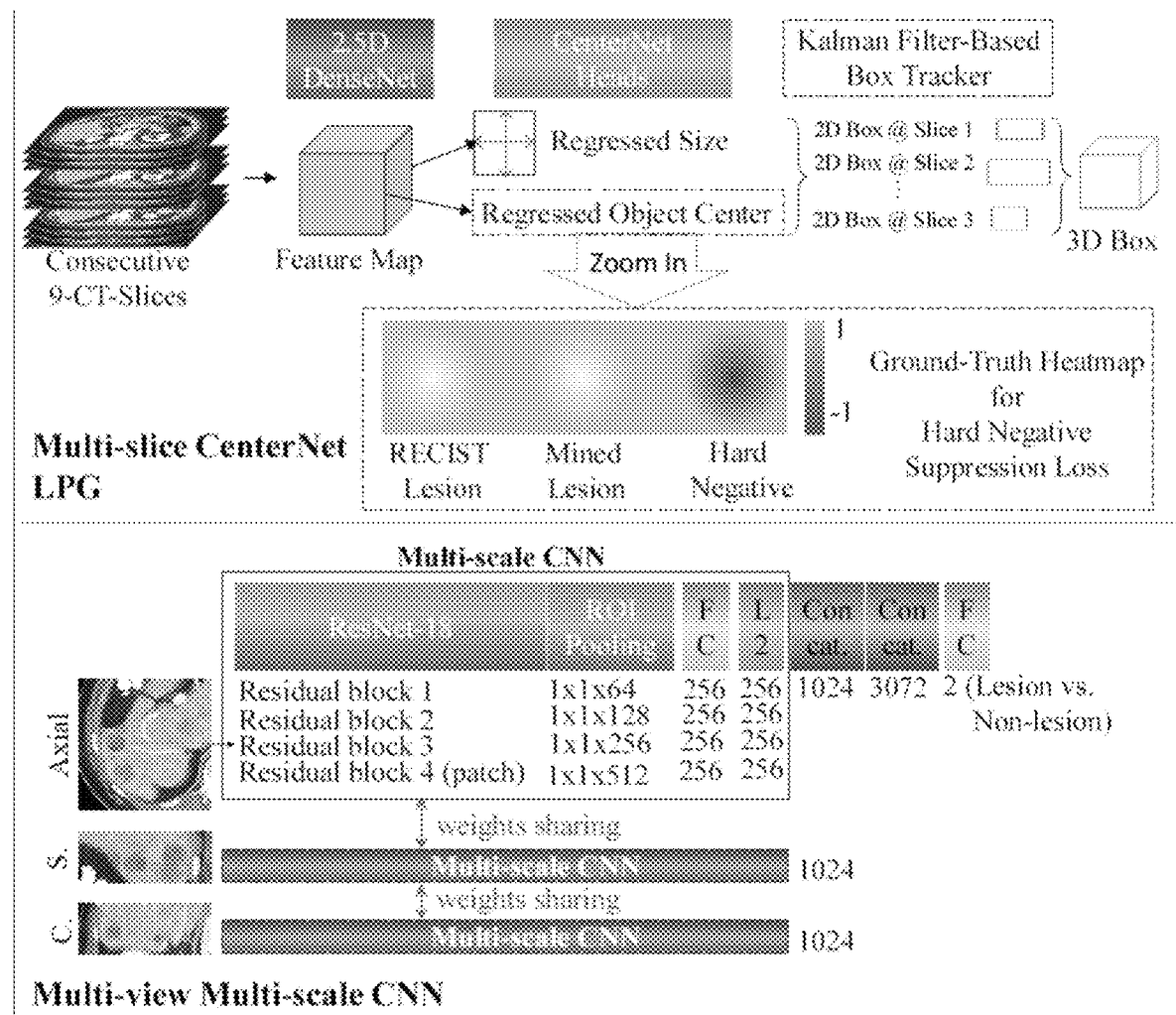
FIG. 7 is a schematic diagram of a 2D-to-3D conversion process in relation to the method of FIG. 2 according one or more embodiments of the present disclosure.

FIG. 7 depicts the 2.5D-LPG, which integrates the 2.5-CenterNet framework with MULAN-style 2.5D context fusion. The LPC is a multi-view multi-scale CNN that processes lesion proposals with axial, sagittal, and coronal views and multiscale CNN feature. The LPC is trained with the RECIST verified proposals, $P_M^R$, $P_M^-$, and $P_H^R$. This combination is expected to be representative to the actual distribution of lesions in DeepLesion. Although the negative samples are only generated from $V_M$, the negative samples are also representative to the actual distribution of hard negatives since the hard negatives are typically healthy body structures which are common across patients.

With the LPC trained, the trained LPC is applied to the proposals needing harvesting: $P_H/P_H^R$. The LPG and LPC may be independently trained, their pseudo-probability outputs may be independent as well. Thus, the final score of a 3D proposal may be calculated as sG,C=sGsC, where sG,C is the final score, sG and sC are objectiveness LPG score and LPC probability, respectively. Based on the proposal scores, positive and negative harvested proposals, $P_H^+$ and $P_H^-$, respectively, are generated, by choosing a threshold, which provides a precision of 60% on the annotated volumes, $V_M$. This produces $P_H^+$. To find more reliable negatives, $P_H^-$ is selected from the remaining proposals whose score is <0.2. These are proposals whose objectiveness scores are high enough to pass the tG threshold. A threshold cutoff other than <0.2 may be adopted dependent upon a given project at hand.

At sub-step S210.6, false-positive lesion objects are removed from the revised first 2D image set according to the 3D composite image to obtain a second-revised first 2D image set. When fusing or stacking of the 2D image slices are performed via the Kalman Filter-based tracker, the tracker stacks proposals basing on their 2D intersection over union (IoU) being greater or equal to 0.5, creating a 3D bounding box $(x_1', x_2', y_1', y_2', z_1', z_2')$. The IoU may be of any suitable values, including but not limited to a value of greater or equal to 0.5. To measure performance, 2D bounding boxes may be generated based on the extents of the RECIST marks, $(x_1, x_2, y_1, y_2, z_1, z_2)$, where z is the slice containing the mark. The 3D box is counted as a true positive if, in certain embodiments, $z_1' \leq z_2'$ and IoU $((x_1, x_2, y_1, y_2), (x_1', x_2', y_1', y_2')) \geq 0.5$. Otherwise, it may be considered a false positive. IoU may vary dependent upon a give project at hand. In certain embodiments, IoU is of a range of between 0 and 1, inclusive, or more particularly, a range of between 0.5 and 0.9, inclusive.

At step S210.8, the second-revised first 2D image set is fed back to the LPG to obtain conditioned LPG. At step S220, the 2.5D-LPG is applied to a second 2D image set different than the first 2D image set to obtain a second set of lesion proposals. As mentioned herein elsewhere, the second 2D image set differs than the first 2D image set at least in that the first 2D image set is subject to manual annotation enhancement by the board-certified radiologists, while the second 2D image set is the remainder of the subset randomly selected from the larger database such as the DeepLesion that has not been subjected to manual annotation enhancement. The goal includes to harvest lesion annotations from the second 2D image set via the 2.5D-LPG trained on the annotation-enhanced first 2D image set.

Proposals from the second 2D image set, such as $V_H$ that cover the original RECIST marks, may be denoted $P_H^R$, which may be used as another source of positives. The original annotations $P_H^R$ are annotations previously present in the DeepLesion relative to the second 2D image set. Of course, these annotations $P_H^R$ are pre-existing and additional to the annotations the 2.5D-LPG is aiming to harvest.

Figure 2A:
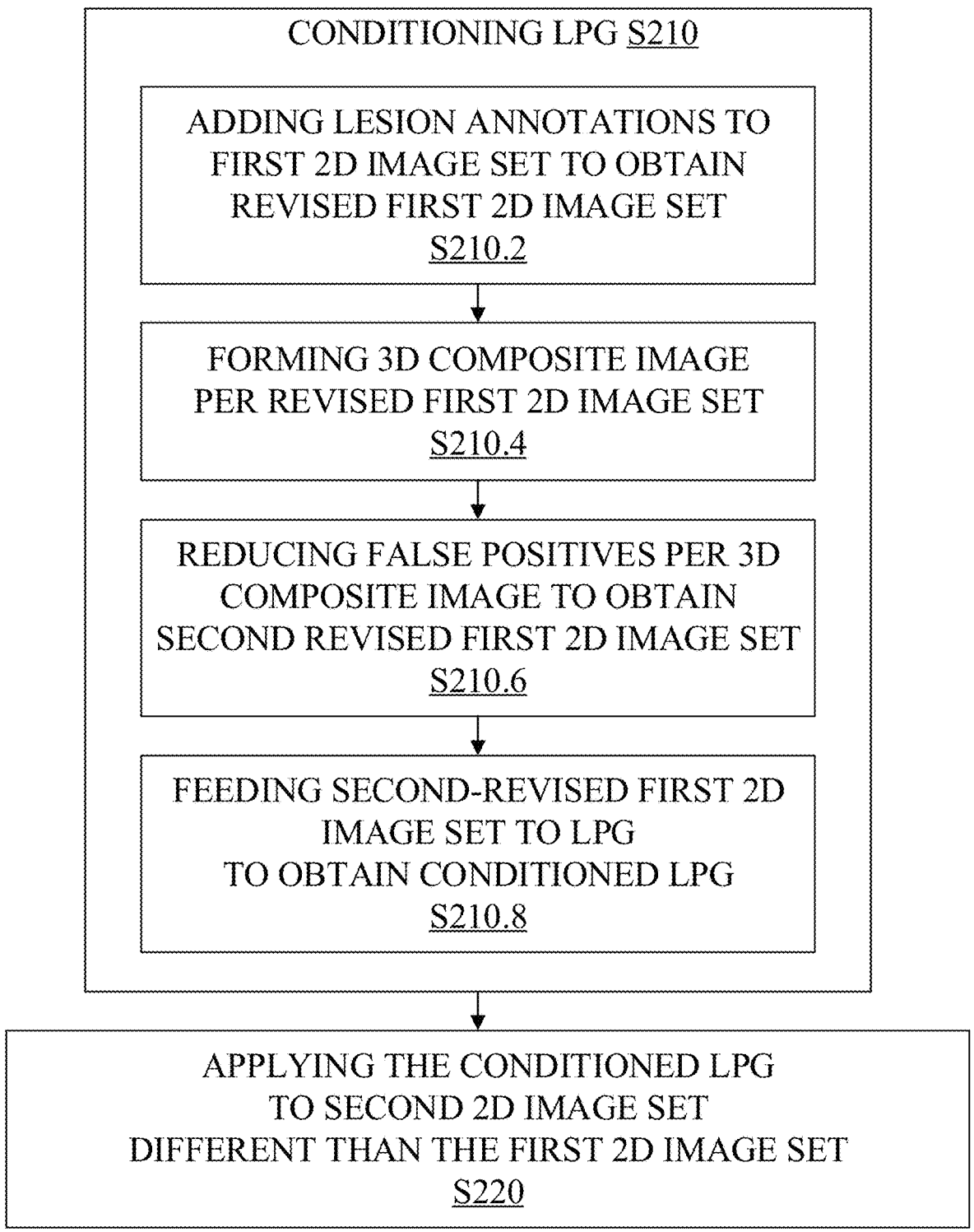
FIG. 2A is a schematic flow chart diagram of a model-training method according to one or more embodiments of the present disclosure.
Figure 2B:
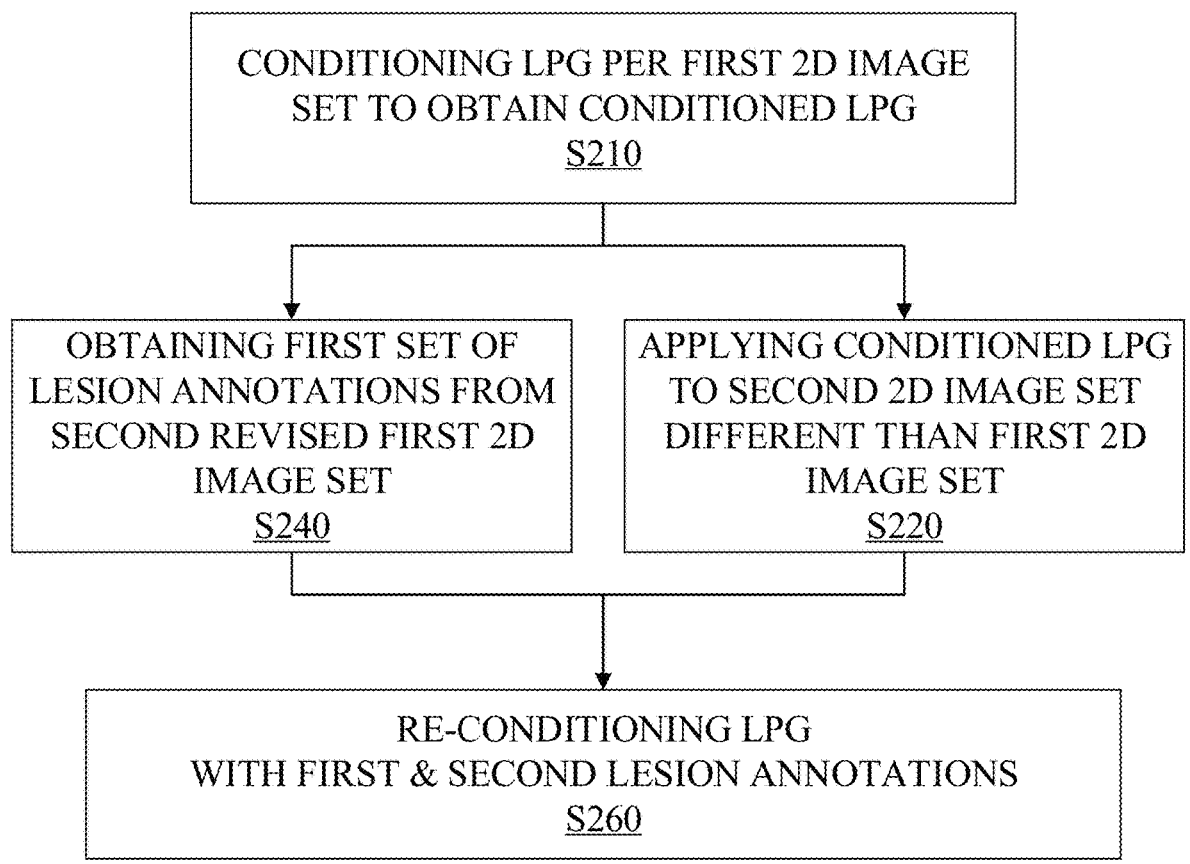
FIG. 2B is a schematic flow chart diagram of a variation to the model-training method of FIG. 2A.

Method 200B of FIG. 2B differs than the method 200A in employing two additional steps, namely step S240 and S260, after step S210. At step S240, a first set of lesion proposals is obtained from the second-revised first 2D image set.

At step S260, the 2.5D LPG is re-trained or re-conditioned with the first and second sets of lesion proposals or annotations to obtain a re-conditioned LPG for harvesting lesion proposals.

In another embodiment of the present disclosure, the first set of lesion proposals may include a first set of true positive lesion proposals and a first set of false positive lesion proposals, and the second-revised first 2D image set is applied to a lesion proposal classifier (LPC) to obtain the first set of true positive lesion proposals and the first set of false positive lesion proposals. Continuing from sub-step S210.2, because $V_M$ refers to the annotation-enhanced first 2D image set, the first set of lesion proposals $P_M$ is divided into true positive and false positive proposals, denoted $P_M^R$ and $P_M^-$, respectively. $P_M^R$, $P_M^-$, and $P_H^R$ are used to train a binary lesion proposal classifier (LPC). Like the LPG, any generic solution may be used; however, and as shown here, a multi-view classification approach is particularly useful. The trained LPC is then used to classify $P_H$ into $P_H^+$ and $P_H^-$, which are the designated positive and negative proposals, respectively.

In certain embodiments, the first image set includes an M image set or M volumes, such as the 744 volumes with enhanced annotations entered by the physician, which is also referred to as $V_M$ referenced in FIG. 12.

In certain embodiments, the second image set includes an H image set or H volumes without enhanced annotations entered by the physician, which may be referred to as $V_H^{test}$ set of 100 volumes or $V_H$ set of 13,231, referenced in FIG. 12.

In certain embodiments, $P_M^R$ refers to a population of proposals, according to the M image set, that can find respective matches in the original RECIST annotations and/or the enhanced annotations entered by the radiologist. $P_M^R$ may thus represent a population of true positives according to the M image set.

In certain embodiments, $P_M^-$ refers to a population of proposals, according to the M image set, that cannot find respective matches in the original RECIST annotations and/or the enhanced annotations entered by the radiologist. $P_M^-$ may thus represent a population of false positives according to the M image set.

In certain embodiments, $P_H^R$ refers to a population of proposals, according to the H image set, that can find respective matches in the original RECIST annotations. $P_H^R$ may thus represent a population of true positives according to the H image set.

In certain embodiments, $P_H^+$ refers to a population of proposals, according to the H image set, that cannot find respective matches in the original RECIST annotations, but are considered positive for having satisfied certain preset conditions. $P_H^R$ may thus represent a population of true positives according to the H image set that are new and additional to the original RECIST annotations.

In certain embodiments, $P_H^-$ refers to a population of proposals, according to the H image set, that cannot find respective matches in the original RECIST annotations and also fail to meet certain preset conditions, and therefore are considered false positives.

With the RECIST verified positive and negative proposals in hand, namely $P_M^R$, $P_M^-$, and $P_H^R$, a next step is to identify the remaining proposals in $V_H$. To do this, the proposals are used to train an LPC. In principle, any classifier may be used, but what is used in this embodiment is a multi-view CNN classifier that incorporates 3D context using axial, coronal, and sagittal slices generated from each proposal CenterPoint. This may be based on the intuition that 3D context helps differentiates true positive lesion proposals from false positives, whether for machines or for clinicians. Such multi-view setups have been shown to boost performance for lesion characterization, and have the virtue of offering a much more computational and memory efficient means to encode 3D context compared to true 3D networks.

FIG. 3 is a schematic flow chart diagram of an alternative to step S210.4 of the method 200A/B referenced in FIG. 2A/B, where the step S210.4 of fusing the revised first 2D image set to form the 3D composite image may include four sub-steps, namely step S310, step S320, step S330, and step S340.

At step S310, 2D bounding boxes are added over annotated lesions in the revised 2D image set. At step S320, the revised first 2D image set may be stacked to one another. The stacking may be performed via any suitable method. A non-limiting example method for stacking is Kalman Filter-based tracker. At step S330, the 2D bounding boxes are fused together after stacking to obtain 3D bounding boxes. At step S340, it is then determined as to whether an annotated lesion is a true positive based on a comparison between the 2D bounding boxes and the 3D bounding boxes.

Figure 9:
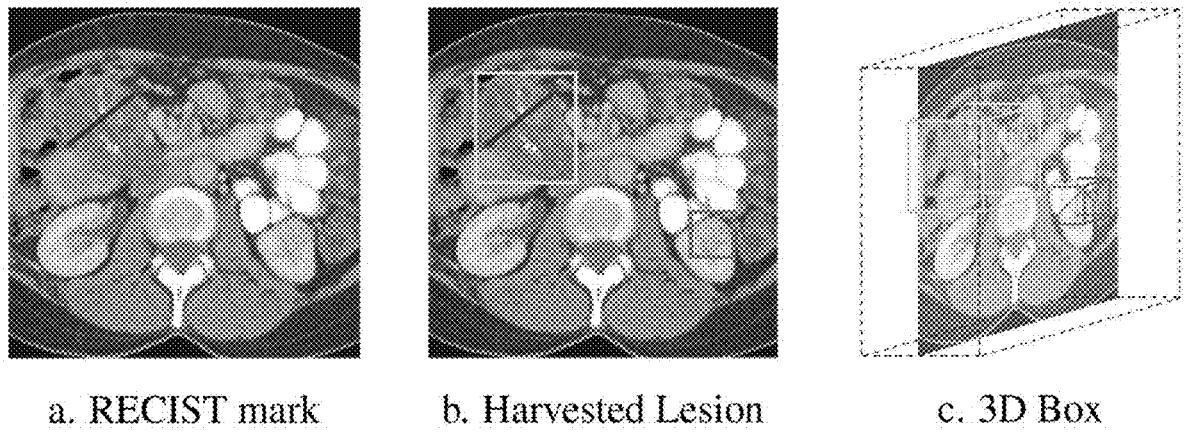
FIG. 9 is a schematic diagram of views of lesion annotations after and before harvesting according to one or more embodiments of the present disclosure.

FIG. 9 shows in 9a) RECIST marks, in 9b) harvested lesions, and in 9c) 3D boxes. FIG. 9a depicts an example 2D RECIST mark covering a lesion. These marks can be incomplete by both not including all lesions, such as missing the lesion annotated in a smaller box shown in FIG. 9b, or by not marking covering the 3D extent of lesions, such as the cubic 3D boxes depicted in FIG. 9c. The present disclosure, in one or more embodiments, is advantageous in uncovering these otherwise missing lesion annotations and providing 3D markings or boxes to these lesion annotations, in a manner exemplified in 9b and 9c of FIG. 9.

FIG. 4 is a schematic diagram of a method 400 representing a variation to the method 200 referenced in FIG. 2. In comparison to the method 200A/B of FIG. 2A/B, the method 400 includes two sub-steps, namely step S420 and step S440, respectively within the context of step S240 and step S260 referenced in FIG. 2B.

As a sub-step to the step S240 of obtaining the first set of lesion annotations from the second-revised first 2D image set, step S420 includes subjecting the second-revised first 2D image set to a lesion proposal classifier (LPC) to obtain the first set of true positive lesion annotations and the first set of true negative lesion annotations. As a sub-step to the step S260 of re-training the 2.5D-LPG with first and second lesion annotations, step S440 includes re-training the 2.5D-LPG with the first sets of true positive and true negative lesion annotations and the second set of lesion annotations.

FIG. 5 is a schematic diagram of a method 500 representing a variation to the method 200A/B referenced in FIG. 2A/B. In comparison to the method 200 of FIG. 2, the method 400 includes two sub-steps, namely step S530 and step S540, respectively within the context of step S220 and step S260 referenced in FIG. 2A/B.

At step S530, the step S220 of applying the 2.5D-LPG to the second 2D image set to obtain second lesion annotations is carried out such that the second set of lesion annotations include a second initial set of lesion annotations prior to application of the 2.5D-LPG and a second harvested set of lesion annotations after application of the 2.5D-LPG. At step S540, the step S260 of re-training the 2.5D-LPG with the first and second lesion annotations further includes re-training the 2.5D-LPG with the first set of lesion annotations, the second initial lesion annotations, and the second harvested lesion annotations.

FIG. 6 is a schematic diagram of a method 600 representing a variation to the method 200A/B referenced in FIG. 2A/B. In comparison to the method 200A/B of FIG. 2A/B, the method 400 includes three sub-steps, namely step S530, step S630, and step S640, respectively within the context of step S220 and step S260 referenced in FIG. 2 A/B.

As a sub-step of the step S220 of applying the 2.5D-LPG to the second 2D image set to obtain second lesion annotations, step S530 is carried out such that the second set of lesion annotations include a second initial set of lesion annotations prior to application of the 2.5D-LPG and a second harvested set of lesion annotations after application of the 2.5D-LPG. At step S630, the step S220 of applying the 2.5D-LPG to the second 2D image set to obtain the second lesion annotations further includes subjecting the second harvested lesion annotations to the LPC to obtain the second harvested true positive and true negative lesion annotations.

At step S640, the step S260 of re-training the 2.5D-LPG with the first and second lesion annotations further includes ret-training the 2.5D-LPG with the first lesion annotations, the second initial lesion annotations, and the second harvested true positive and true negative lesion annotations.

Figure 8:
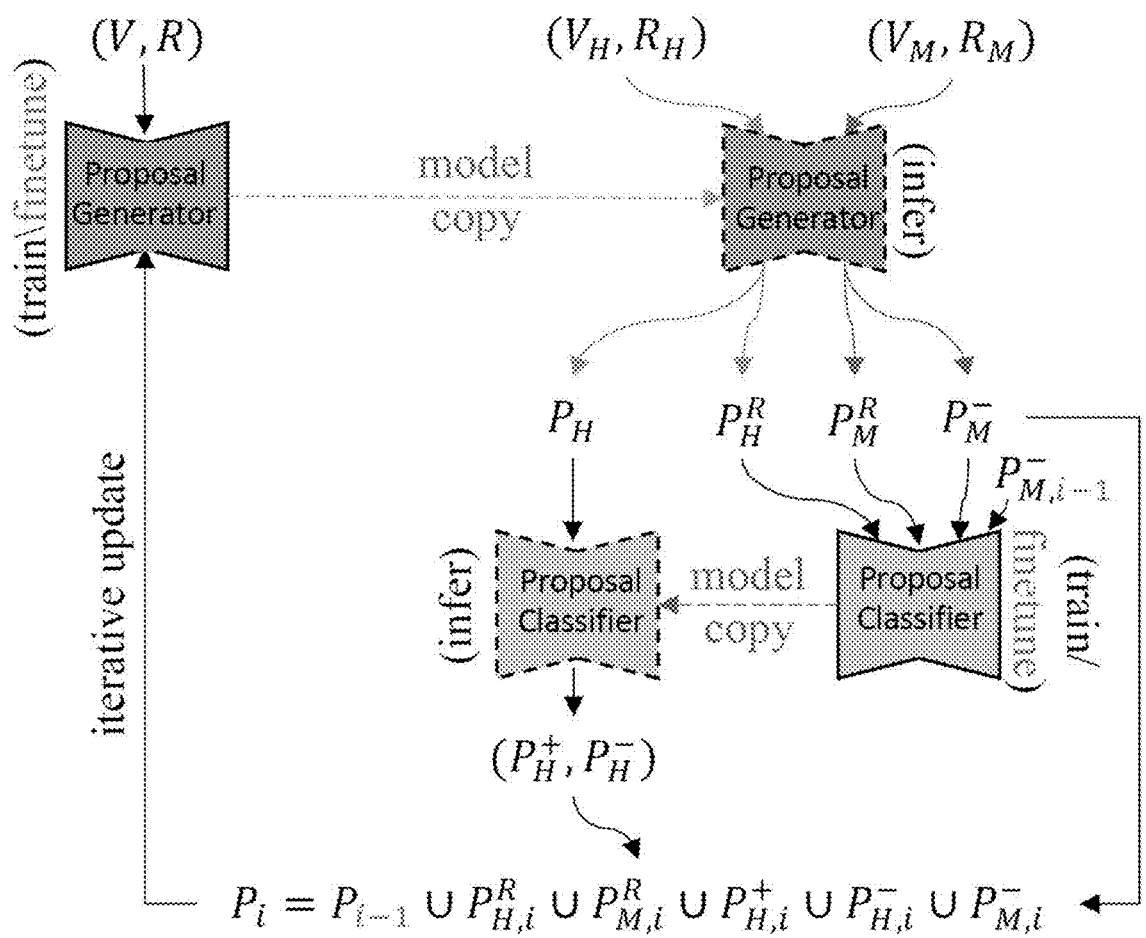
FIG. 8 is a schematic diagram presenting the method of FIG. 2 in a framework view according to one or more embodiments of the present disclosure.

FIG. 8 is a schematic diagram depicting a framework of the method 200 A/B of FIG. 2 A/B, where the subscript i−1 indicates data from the former iteration if i is greater than 1, otherwise the corresponding sets, $P_{i-1}$ and $P_{M,i-1}^-$, are empty. This framework shows the iterative label completion approach via which a set of newly harvested positive and negative 3D proposals, $P = P_H^+ \cup P_H^- \cup P_{HR}^U P_M^R \cup P_M^-$, are uncovered. To refine the process further, P is then used to generate 2D slice-wise bounding boxes. Along with the original RECIST marks, R, these 2D bounding boxes may then be used to finetune the original 2D LPG and have the process begin anew. For the purpose of re-training the LPG, $P_M^-$ and $P_H^-$ are used for hard or true negatives. Each round, i, provides a set of harvested proposals, $P_{H,i}^+$. In addition, $P_{M,i}^R$ and $P_{H,i}^R$ provide 3D bounding boxes for lesions that have previously been only annotated with 2D RECIST marks. Thus, this iteration process generates a more complete and richly annotated dataset. For brevity and clarity, the i is skipped in some of the formulas and equations presented herein.

The iterative updating may be performed as follows. After a round of harvesting, the process is repeated by finetuning the LPG, but with two differences. First, additional 2D slices and accompanying bounding boxes may be obtained in view of the 3D proposals available at hand, and these additional 2D slices and accompanying bounding boxes are fed into training. Second, mined lesions and hard negatives are incorporated to further improve the proposal generation. For hard negative mining, selected from $P_H^-$ and $P_M^-$ are any proposals whose objectiveness score p(x|G) is >0.5, which selects for challenging instances to the proposal generator. To keep computational demands reasonable, only the 2D slides with certain objectiveness score within each proposal of $P_M^R \cup P_M^- \cup P_H^R \cup P_H^+ \cup P_H^-$ are used.

To incorporate harvested and hard negative proposals, while the same procedure is adopted, separate heat maps are created for positive (RECIST-marked or harvested) and hard-negative lesions. These are denoted $Y_{XY}^P$ and $Y_{xy}^n$, respectively. A master ground truth heat map, $Y_{xy}$, by overwriting $Y_{XY}^P$ with $Y_{xy}^n$:

$$Y_{xy} = \begin{cases} -Y_{xy}^n & \text{if } Y_{xy}^n > 0 \\ Y_{xy}^p & \text{otherwise} \end{cases}.$$

The result is a ground truth map that can range from [−1, 1]. This process is performed to reduce or eliminate false positive rates. The ground truth heatmaps may be visualized to differentiate among a RECIST lesion, a mined lesion, and a hard negative.

Figure 10:
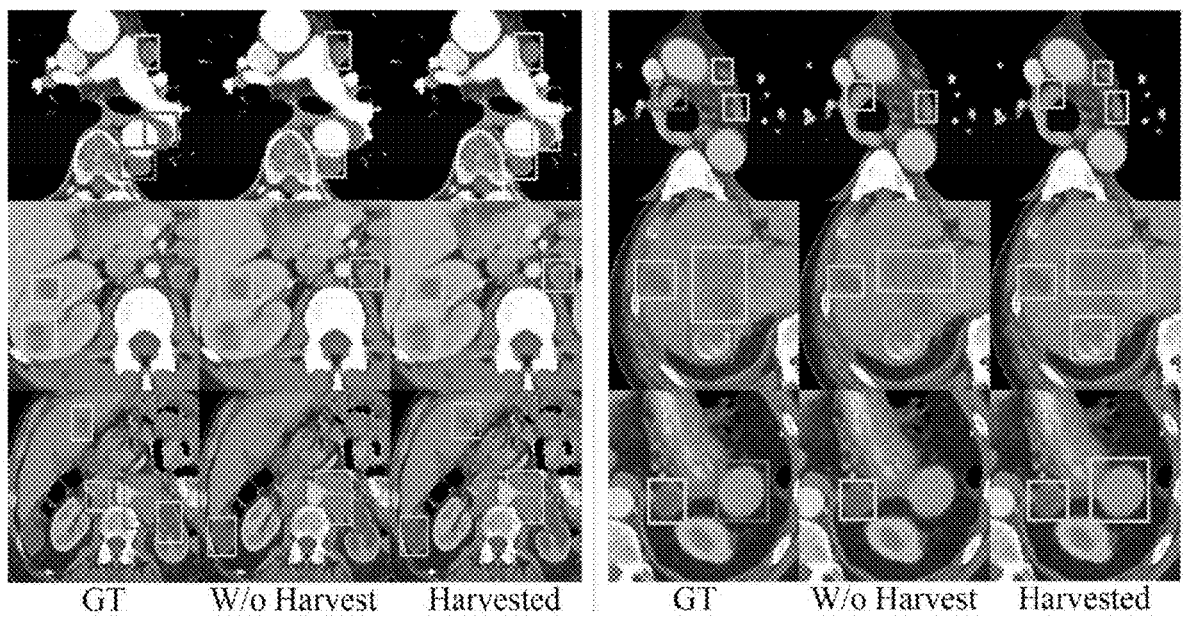
FIG. 10 is a schematic diagram of views of lesions annotations after and before harvesting according to one or more embodiments of the present disclosure.

FIG. 10 provides some visual examples of the harvested lesions. As can be seen, some of the lesions missing from the original RECIST marks are harvested and represented in some of the bounding boxes. These results demonstrate the utility and power of the lesion harvesting approached described herein.

Figure 11:
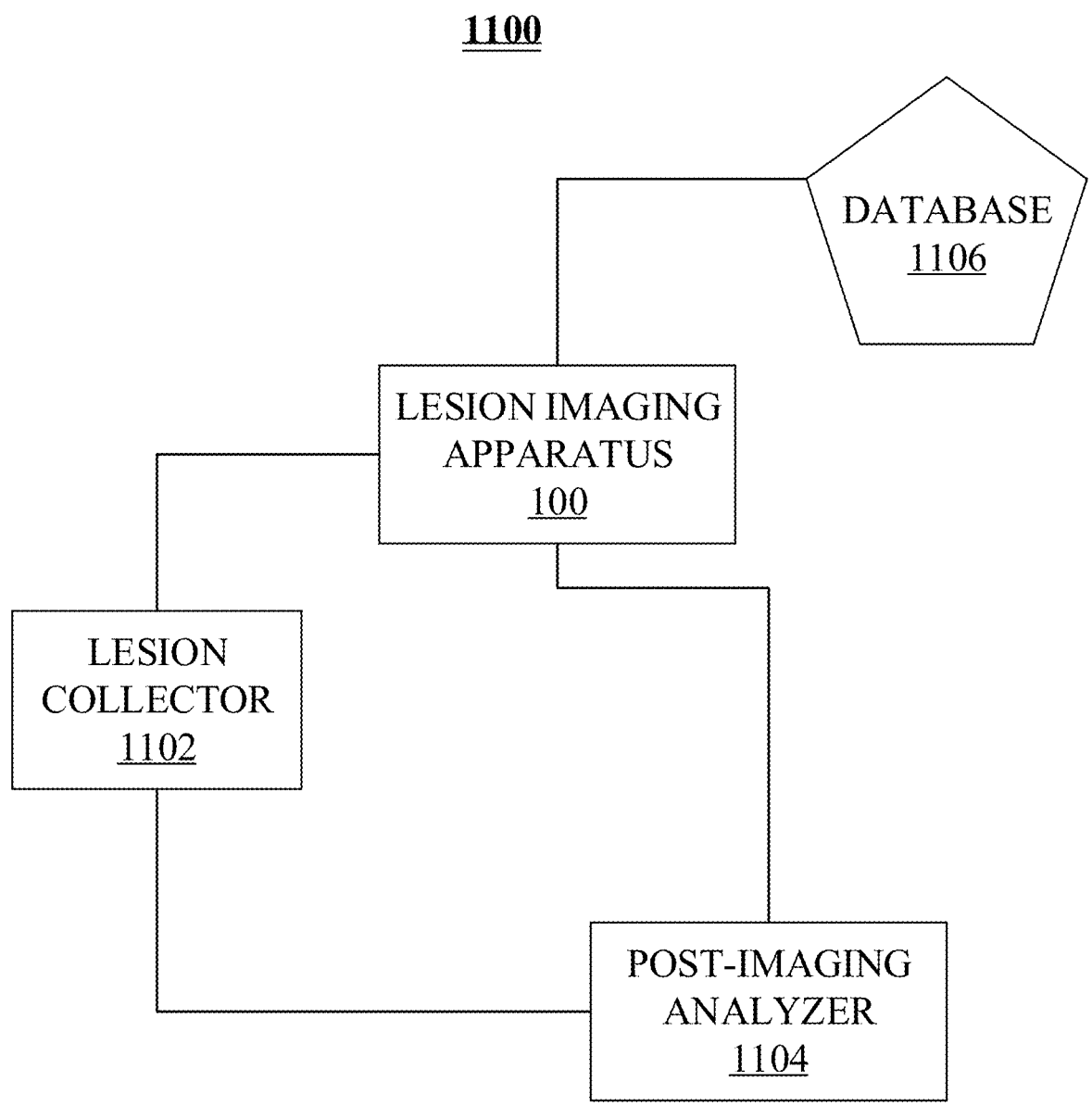
FIG. 11 is a schematic diagram of a lesion imaging system employing the apparatus of FIG. 1 according to one or more embodiments of the present disclosure.

FIG. 11 is a schematic view of a lesion imaging system 1100 according to one or more embodiments of the present disclosure. The lesion imaging system 1100 may include the apparatus 100 of FIG. 1, in communication with a lesion collector 1102. The lesion collector 1102 may store and provide raw image data on lesion slices. These lesion slices may be previously obtained via any suitable biopsy equipment via, for example, in-patient or out-patient surgeries. In certain embodiments, the lesion collector 1102 may itself be a temperature-controlled tissue collector that store raw lesion samples from which lesion images may be taken. These images data and/or the raw lesion samples as maybe stored at the lesion collector 1102 are in a form or of specifications that particularly suitable for image processing at the apparatus 100.

Referring back to FIG. 11, and in certain embodiments, the lesion imaging system 100 may further include a post-imaging analyzer 1104 which receives imaging output from the apparatus 100 and makes a determination as to whether additional lesion samples need to be inputted from the lesion collector 1102 to the apparatus 100 for retrieval of additional imaging data. The post-imaging analyzer 1104 may be a stand-alone computing device or in certain embodiments an integral part of the apparatus 100.

The apparatus 100, the lesion collector 1102 and the post-imaging analyzer 1104 may be in communication with each other via any suitable data transmission, for example, via wireless or wireless internet communications. In certain embodiments, the apparatus 100 may further be in data communication with a lesion image database 1106, whether public or private, such as the DeepLesion, to supplement and/or update these databases per any particular data-sharing agreements. Of course, the database 1106 may be made private for fee-based sharing, and the database 1106 may be outputted in any suitable form such as data disks and data patches.

Going back to FIG. 1, the processor 102 may include any appropriate processor(s). In certain embodiments, processor 102 may include multiple cores for multi-thread or parallel processing. Processor 102 may execute sequences of computer program instructions to perform various processes, such as method 200 A/B of FIG. 2 A/B. Storage medium 104 may be a non-transitory computer-readable storage medium, and may include memory modules, such as ROM, RAM, flash memory modules, and erasable and rewritable memory, and mass storages, such as CD-ROM, U-disk, and hard disk, etc. The communication module 108 may include network devices for establishing connections through a network. Display may include any appropriate type of computer display device or electronic device display (e.g., CRT or LCD based devices, touch screens). Peripherals 112 may include additional I/O devices, such as a keyboard, a mouse, and so on. The processor 102 may be configured to execute instructions stored on the storage medium 104 and perform various operations related to a method of harvesting lesion annotations such as method 200 A/B of FIG. 2 A/B.

In certain particular embodiments, and to harvest lesions from the DeepLesion dataset, 844 volumes of lesion images are randomly selected from the original 14075 training CTs. The 844 randomly selected volumes of 2D images or volumes are then annotated by a board-certified radiologist. Of these, 744 volumes are selected as $V_M$, corresponding to about 5.3% of the 14,075 total volumes of the training CTs, and the remainder 100 volumes are designated as an evaluation set for lesion harvesting. The remainder 100 are treated as $V_H^{test}$.

After convergence, level of precision is measured and the harvested lesions are recalled. In addition, detection performance is measured on systems trained on the harvested lesions by annotating 35% of the testing CT volumes. These volumes, denoted $V_D^{test}$ as referenced in FIG. 12, are a set of testing volumes not previously seen in the harvesting framework. However, due to the RECIST guidelines and workload limits, clinicians typically mark only a small number of lesions per CT scan as the finding of interest. Often CT images exhibit multiple co-existing lesions per patient. This challenges developing high-fidelity disease detection algorithms and artificially limits the dataset's usefulness for biomarker development. Nevertheless, it is impractical and infeasible to recruit clinicians to manually revise and add back annotations for the entire dataset.

The lesion harvesting system is run on $V_D^{test}$ for a number of rounds such as 3 rounds. As may be observed in Table 1, the original RECIST marks only have a recall of 36.4%, with an assumed precision of 100%. However, after one run or one iteration, the initial lesion proposals already boost the recall to 48.9%, while keeping the precision at 90%. After filtering with the lesion proposal classifier, this recall is boosted to 54.5%, representing a roughly 20% increase in recall over the original RECIST marks and demonstrating the power and usefulness of the cascaded LPG and LPC approach. After 3 rounds of run of the system, the performance increases further, topping out at 61.3% recall at 90% precision. This corresponds to harvesting 9,805 more lesions from the 21791 original RECIST marks. Moreover, 2D lesion bounding boxes are also converted to 3D. It should be stressed that these results are obtained by annotating 744 volumes, which represents only 5.3% of the original data.

TABLE 1

Recalls of lesion label sets at various precision levels

| Label Set | R@80% | R@85% | R@90% | R@95% |
|---|---|---|---|---|
| R | | | 0.364 @ 100% | |
| R U $P_{H,1}$ | 0.560 | 0.509 | 0.489 | 0.476 |
| R U $P_{H,1}^+$ | 0.591 | 0.572 | 0.545 | 0.497 |
| R U $P_{H,2}^+$ | 0.678 | 0.651 | 0.585 | 0.512 |
| R U $P_{H,3}^+$ | 0.668 | 0.649 | 0.613 | 0.498 |

In certain embodiments, the term "recall" refers to a value in percentage of every 100 confirmed annotations, how many of such annotations may be discovered using the annotation-harvesting method. For example, a 50% recall value indicates that for every 100 confirmed or true annotations, such as annotation confirmed by the physician, 50 of these 100 can be uncovered by the annotation-harvesting method.

In certain embodiments, the term "precision" refers to a value in percentage of every 100 proposals generated by the annotation-harvesting method, how many of these 100 proposals are true and/or confirmed annotations. For example, a 50% precision level indicates that for every 100 proposals generated by the annotation-harvesting method, 50 of the 100 find respective matches in the annotations confirmed by the physician and/or are found to meet certain preset conditions as true positives.

As can be seen from Table 1, the recall of the original annotation, for example, as depicted with "R," is 36.4%, which means the original annotation is 36.4% of the enhanced annotation, while the enhanced annotation may be considered theoretical complete annotation had the annotations been identified and entered by a trained professional or professionals. In comparison, the results after the 3 rounds of run, for example, identified in the last row of Table 1, show the recall of 61.3% at a precision of 90%, which means the corresponding annotation is 61.3% of the enhanced annotation. Compared with the original annotation, the 3 rounds of run show a 24.9% increase of recall making the annotation to be more complete.

Table 2 presents the contributions of each variant of the harvested lesions to training the LPG. When including the manually annotated proposals, $P_M^R$, the performance does not improve much over simply using the original RECIST marks. This reflects the relatively small size of $P_M^R$ compared to the entire dataset, which is about 5.3% as mentioned above. However, larger impacts may be seen when LPG-conditioning includes the hard negatives, $P_M^-$, from the dataset $V_M$, which is additionally annotated by the board-certified clinicians. When including the hard negatives from the volumes needing harvesting, for example, $P_H^-$, performance boosts are greater. This validates the hard-negative mining approach. Interestingly, the addition of extra positive samples, $P_H^+$ and $P_H^R$, do not contribute much to the recall at low precision end.

is also performed on the 2.5D-CenterNet LPG, except the 2.5D-CenterNet is trained as a detector. Both detector variants are tested on the unseen $V_D^{test}$ data. As Table 4 demonstrates, using the harvested lesions to train detectors provide boosts in recall and precision. The extra mined lesions $P_H^+$ boosts MULAN's detection performance by 4% in AP. These results help demonstrate the importance and impact of harvesting missing annotations. Finally, it is also noted that 2.5D-CenterNet can outperform MULAN, further validating the LPG design choices and suggesting that the innovations explored here may also progress the important topic of lesion detection. Compared with Table 2, 2.5D-CenterNet follows the same trajectory here that gains a higher recall at the very high precision (same as low FPs) end, where is the operation point for accepting lesion detection results.

TABLE 2

Lesion proposal generation trained with different label sets. The UB column presents the highest possible recall with all proposals considered.

| Exp. | R | $P_M^R$ | $P_M^-$ | $P_H^R$ | $P_H^+$ | $P_H^-$ | iter. | Recall @ FPs [0.125, 0.25, 0.5, 1, 2, 4, 8, 16]/Volume | | | | | | | | UB |
|---|---|---|---|---|---|---|---|---|---|---|---|---|---|---|---|---|
| (a) | ✓ | | | | | | 1 | 0.120 | 0.210 | 0.317 | 0.457 | 0.531 | 0.610 | 0.669 | 0.729 | 0.936 |
| (b) | ✓ | ✓ | | | | | 1 | 0.160 | 0.217 | 0.329 | 0.443 | 0.557 | 0.626 | 0.695 | 0.752 | 0.948 |
| (c) | ✓ | ✓ | ✓ | | | | 2 | 0.195 | 0.274 | 0.369 | 0.488 | 0.555 | 0.648 | 0.705 | 0.752 | 0.945 |
| (d) | ✓ | ✓ | ✓ | ✓ | | | 2 | 0.179 | 0.312 | 0.455 | 0.524 | 0.605 | 0.662 | 0.726 | 0.779 | 0.945 |
| (e) | ✓ | ✓ | ✓ | ✓ | ✓ | | 2 | 0.289 | 0.355 | 0.455 | 0.531 | 0.576 | 0.652 | 0.707 | 0.757 | 0.950 |
| (f) | ✓ | ✓ | ✓ | ✓ | ✓ | ✓ | 2 | 0.304 | 0.386 | 0.471 | 0.536 | 0.586 | 0.626 | 0.683 | 0.733 | 0.943 |
| (g) | ✓ | ✓ | ✓ | ✓ | ✓ | ✓ | 3 | 0.255 | 0.388 | 0.471 | 0.543 | 0.595 | 0.641 | 0.717 | 0.767 | 0.952 |

In addition to demonstrating the utility of the lesion harvesting approach, choice of LPG is also analyzed and justified. To do this, the 2.5D-CenterNet is compared against MULAN, the current state-of-the-art detector for DeepLesion. As can be seen from Table 3, compared to MULAN, the 2.5D-CenterNet is more sensitive to lesions and is more efficient. At rates of 0.125 to 16 false positives(s) per volume, the LPG outperforms MULAN with 9% to 1.2% recall. On average, it also runs 50% faster than MULAN, which is an important factor within the larger lesion harvesting framework. These results help validate the choice of LPG and demonstrate the improvement with considerable gains in performance.

TABLE 3

Lesion proposal generators evaluated on $V_H^{test}$ at the first iteration.

| Method | Recall @ FPs [0.125, 0.25, 0.5, 1, 2, 4, 8, 16]/Volume | | | | | | | | UB | speed |
|---|---|---|---|---|---|---|---|---|---|---|
| MULAN | 0.070 | 0.124 | 0.226 | 0.333 | 0.474 | 0.560 | 0.669 | 0.733 | 0.924 | 1.08 s/volume |
| 2.5D-CenterNet | 0.160 | 0.217 | 0.329 | 0.443 | 0.557 | 0.626 | 0.695 | 0.752 | 0.948 | 0.66 s/volume |

The choice of multi-view LPC is also validated. To do this, the performance of lesion classification evaluated on $P_H^{test}$ is compared at the first iteration of the method. A comparison among 2D, multi-view, and 3D versions of ResNet-18 is conducted, and results are compared when using the objectiveness, classification, or the final proposal score, for example, sG, sC, or sG,C, respectively. Out of all options, the multi-view approach works best. In addition to its high performance, it also has the virtue of being much simpler and faster than a full 3D approach. All supports the choice of a multi-view LPC.

To demonstrate the benefits of the harvested lesions, the state-of-the-art MULAN detector is trained on the original DeepLesion RECIST marks and then is re-trained with the addition of the harvested lesions, $P_H^+$. The same experiment

TABLE 4

Evaluation of detectors trained with and without mined lesions on $V_D^{test}$.

| Detector | R | $P_H^+$ | R@FPs [0.125, 0.25, 1] | | | AP |
|---|---|---|---|---|---|---|
| CenterNet | ✓ | | 0.113 | 0.161 | 0.290 | 0.422 |
| CenterNet | ✓ | ✓ | 0.106 | 0.165 | 0.297 | 0.418 |

TABLE 4-continued

Evaluation of detectors trained with and without mined lesions on $V_D^{test}$.

| Detector | R | $P_H^+$ | R@FPs [0.125, 0.25, 1] | | | AP |
|---|---|---|---|---|---|---|
| MULAN | ✓ | | 0.072 | 0.132 | 0.316 | 0.394 |
| MULAN | ✓ | ✓ | 0.105 | 0.162 | 0.365 | 0.434 |
| 2.5D-LPG | ✓ | | 0.118 | 0.183 | 0.387 | 0.487 |
| 2.5D-LPG | ✓ | ✓ | 0.132 | 0.189 | 0.369 | 0.474 |

As shown above, a framework is presented to harvest lesions from datasets such as $V_H$. By leveraging a reasonably small subset of annotation-enhanced data (5.3%), and by chaining together an LPG and LPC, unlabeled lesions are iteratively discovered and exploited. Moreover, harvested and hard negatives proposals may be incorporated to iteratively improve the harvesting process. The LPG of 2.5D-CenterNet is present to enhance performance further, which offers important improvements over the current state-of-the-art MULAN detector.

Table 5 shows, when the original test metrics for DeepLesion are employed, which only evaluate on the RECIST slices, it is still manageable to achieve the current state-of-art detection (the comparable) performance for this dataset. Implementation of MULAN performs 84.9% average detection sensitivity, which is 1.2% lower than the comparable. However, in order to achieve 86.1% average sensitivity, the comparable utilized not only detection but also tagging and segmentation supervisions to train MULAN. Even so, it is worth stressing that the full 3D evaluations on $V_D^{test}$ offer a more accurate assessment of detection performance. These results help demonstrate the impact of harvesting missing annotations.

TABLE 5

Evaluation of detectors conditioned with and without mined lesions

| Detector | R | $P_H^+$ | R@FPs[0.5, 1, 2, 4] | | | | mean |
|---|---|---|---|---|---|---|---|
| CenterNet | ✓ | | 0.680 | 0.773 | 0.838 | 0.883 | 0.794 |
| CenterNet | ✓ | ✓ | 0.681 | 0.774 | 0.840 | 0.881 | 0.794 |
| MULAN | ✓ | | 0.764 | 0.831 | 0.882 | 0.918 | 0.849 |
| MULAN | ✓ | ✓ | 0.768 | 0.835 | 0.883 | 0.920 | 0.852 |
| 2.5D-LPG | ✓ | | 0.780 | 0.852 | 0.894 | 0.922 | 0.862 |
| 2.5D-LPG | ✓ | ✓ | 0.782 | 0.848 | 0.889 | 0.920 | 0.860 |

Although the present disclosure has been shown and described with reference to specific exemplary embodiments thereof, those skilled in the art will understand that, without departing from the spirit and scope of the present disclosure as defined by the appended claims and their equivalents, various changes in form and detail may be made to the present disclosure. Therefore, the scope of the present disclosure should not be limited to the embodiments described above, but should be determined not only by the appended claims, but also by the equivalents of the appended claims.

What is claimed is:

1. A method of harvesting lesion annotations, comprising:
conditioning a lesion proposal generator (LPG) based on a first two-dimensional (2D) image set to obtain a conditioned LPG, including:
adding lesion annotations to the first 2D image set to obtain a revised first 2D image set; forming a three-dimensional (3D) composite image according to the revised first 2D image set; reducing false-positive lesion annotations from the revised first 2D image set according to the 3D composite image to obtain a second-revised first 2D image set; and feeding the second-revised first 2D image set to the LPG to obtain the conditioned LPG;
applying the conditioned LPG to a second 2D image set different than the first 2D image set, to obtain a second set of lesion annotations that includes a second initial set of lesion annotations existing prior to applying the conditioned LPG and a second harvested set of lesion annotations after applying the conditioned LPG,
subjecting the second harvested set of lesion annotations to a lesion proposal classifier (LPC) to obtain a second harvested set of positive lesion annotations and a second harvested set of negative lesion annotations;
obtaining a first set of lesion annotations from the second-revised first 2D image set; and
feeding the first set of lesion annotations, the second initial set of lesion annotations, and the second harvested sets of positive and negative lesion annotations to the conditioned LPG to obtain a re-conditioned LPG for harvesting lesion annotations.

2. The method of claim 1, wherein reducing false-positive lesion annotations from the revised first 2D image set according to the 3D composite image includes:
adding 2D bounding boxes over annotated lesions in the revised first 2D image set;
stacking the revised first 2D image set;
fusing the 2D bounding boxes after stacking to obtain 3D bounding boxes;
determining if a lesion annotation is a false-positive according to a comparison between the 2D bounding boxes and the 3D bounding boxes; and
marking the lesion annotation as negative to reduce false-positive lesion annotations from the revised first 2D image set.

3. The method of claim 1, further comprising:
obtaining a first set of lesion annotations from the second-revised first 2D image set and subjecting the first set of lesion annotations to a lesion proposal classifier (LPC) to obtain a first set of positive lesion annotations and a first set of negative lesion annotations; and
feeding the first sets of positive and negative lesion annotations to the LPC to obtain a conditioned LPC.

4. The method of claim 1, further comprising:
feeding a second set of positive lesion annotations and a second set of negative lesion annotations to a lesion proposal classifier (LPC) to obtain a conditioned LPC.

5. The method of claim 1, wherein the second 2D image set is smaller in image count than the first 2D image set.

6. A lesion imaging system, comprising a lesion proposal generator (LPG) for harvesting lesion annotations, the LPG including a memory and a processor coupled to the memory, the processor being configured to perform:
conditioning the LPG based on a first two-dimensional (2D) image set to obtain a conditioned LPG, including:
adding lesion annotations to the first 2D image set to obtain a revised first 2D image set; forming a three-dimensional (3D) composite image according to the revised first 2D image set; reducing false-positive lesion annotations from the revised first 2D image set according to the 3D composite image to obtain a second-revised first 2D image set; and feeding the second-revised first 2D image set to the LPG to obtain the conditioned LPG;
applying the conditioned LPG to a second 2D image set different than the first 2D image set, to obtain a second set of lesion annotations that includes a second initial set of lesion annotations existing prior to applying the conditioned LPG and a second harvested set of lesion annotations after applying the conditioned LPG,
subjecting the second harvested set of lesion annotations to a lesion proposal classifier (LPC) to obtain a second harvested set of positive lesion annotations and a second harvested set of negative lesion annotations;
obtaining a first set of lesion annotations from the second-revised first 2D image set; and
feeding the first set of lesion annotations, the second initial set of lesion annotations, and the second harvested sets of positive and negative lesion annotations to the conditioned LPG to obtain a re-conditioned LPG for harvesting lesion annotations.

7. The lesion imaging system of claim 6, wherein reducing false-positive lesion annotations from the revised first 2D image set according to the 3D composite image includes:
adding 2D bounding boxes over annotated lesions in the revised first 2D image set;
stacking the revised first 2D image set;
fusing the 2D bounding boxes after stacking to obtain 3D bounding boxes;
determining if a lesion annotation is a false-positive according to a comparison between the 2D bounding boxes and the 3D bounding boxes; and
marking the lesion annotation as negative to reduce false-positive lesion annotations from the revised first 2D image set.

8. The lesion imaging system of claim 6, further comprising: a lesion proposal classifier (LPC), wherein the processor is further configured to perform:
obtaining a first set of lesion annotations from the second-revised first 2D image set and subjecting the first set of lesion annotations to the LPC to obtain a first set of positive lesion annotations and a first set of negative lesion annotations; and
feeding the first sets of positive and negative lesion annotations to the LPC to obtain a conditioned LPC.

9. The lesion imaging system of claim 6, further comprising a lesion proposal classifier (LPC), wherein the processor is further configured to perform:
feeding a second set of positive lesion annotations and a second set of negative lesion annotations to the LPC to obtain a conditioned LPC.

10. A non-transitory computer-readable storage medium storing a plurality of instructions, and when being executed, the plurality of instructions cause a processor to perform:
conditioning a lesion proposal generator (LPG) based on a first two-dimensional (2D) image set to obtain a conditioned LPG, including: adding lesion annotations to the first 2D image set to obtain a revised first 2D image set; forming a three-dimensional (3D) composite image according to the revised first 2D image set; reducing false-positive lesion annotations from the revised first 2D image set according to the 3D composite image to obtain a second-revised first 2D image set; and feeding the second-revised first 2D image set to the LPG to obtain the conditioned LPG;
applying the conditioned LPG to a second 2D image set different than the first 2D image set, to obtain a second set of lesion annotations that includes a second initial set of lesion annotations existing prior to applying the conditioned LPG and a second harvested set of lesion annotations after applying the conditioned LPG,
subjecting the second harvested set of lesion annotations to a lesion proposal classifier (LPC) to obtain a second harvested set of positive lesion annotations and a second harvested set of negative lesion annotations;
obtaining a first set of lesion annotations from the second-revised first 2D image set; and
feeding the first set of lesion annotations, the second initial set of lesion annotations, and the second harvested sets of positive and negative lesion annotations to the conditioned LPG to obtain a re-conditioned LPG for harvesting lesion annotations.

11. The non-transitory computer-readable storage medium of claim 10, wherein reducing false-positive lesion annotations from the revised first 2D image set according to the 3D composite image includes:
adding 2D bounding boxes over annotated lesions in the revised first 2D image set;
stacking the revised first 2D image set;
fusing the 2D bounding boxes after stacking to obtain 3D bounding boxes;
determining if a lesion annotation is a false-positive according to a comparison between the 2D bounding boxes and the 3D bounding boxes; and
marking the lesion annotation as negative to reduce false-positive lesion annotations from the revised first 2D image set.

12. The non-transitory computer-readable storage medium of claim 10, wherein the processor is further configured to perform:
obtaining a first set of lesion annotations from the second-revised first 2D image set and subjecting the first set of lesion annotations to a lesion proposal classifier (LPC) to obtain a first set of positive lesion annotations and a first set of negative lesion annotations; and
feeding the first sets of positive and negative lesion annotations to the LPC to obtain a conditioned LPC.

13. The non-transitory computer-readable storage medium of claim 10, wherein the processor is further configured to perform:
feeding a second set of positive lesion annotations and a second set of negative lesion annotations to a lesion proposal classifier (LPC) to obtain a conditioned LPC.

14. The non-transitory computer-readable storage medium of claim 10, wherein the second 2D image set is smaller in image count than the first 2D image set.

* * * * *